(12) United States Patent
Zerella et al.

(10) Patent No.: US 7,009,074 B2
(45) Date of Patent: Mar. 7, 2006

(54) PROCESS FOR DIRECT OXIDATION OF METHANE TO ACETIC ACID

(75) Inventors: Mark Zerella, Berkeley, CA (US); Sudip Mukhopadhyay, Williamsville, NY (US); Alexis T. Bell, Oakland, CA (US); John Glenn Sunley, East Yorkshire (GB); Sander Gaemers, Bishop Burton (GB); Philip Howard, East Yorkshire (GB); Brian Ellis, Cottingham (GB); Andrew Richard Lucy, Brough (GB)

(73) Assignees: The Regents of the University of California, Oakland, CA (US); BP Chemicals Limited, Middlesex (GB)

( * ) Notice: Subject to any disclaimer, the term of this patent is extended or adjusted under 35 U.S.C. 154(b) by 0 days.

(21) Appl. No.: 10/901,643

(22) Filed: Jul. 28, 2004

(65) Prior Publication Data

US 2006/0025628 A1    Feb. 2, 2006

(51) Int. Cl.
C07C 51/14    (2006.01)
(52) U.S. Cl. .................................................. 562/522
(58) Field of Classification Search ............... 562/522, 562/607
See application file for complete search history.

(56) References Cited

U.S. PATENT DOCUMENTS

| 5,281,752 | A * | 1/1994 | Fujiwara et al. ............ 562/522 |
| 6,383,977 | B1 | 5/2002 | Karim et al. |
| 6,399,816 | B1 | 6/2002 | Borchert et al. |
| 6,472,558 | B1 | 10/2002 | Key et al. |
| 6,706,919 | B1 | 3/2004 | Obana et al. |
| 2003/0158440 | A1 | 8/2003 | Zeyss et al. |
| 2003/0204107 | A1 | 10/2003 | Daniel et al. |
| 2004/0031084 | A1 | 2/2004 | Cook et al. |

FOREIGN PATENT DOCUMENTS

| GB | 226248 | 12/1924 |
| WO | 96/05163 A1 | 2/1996 |

OTHER PUBLICATIONS

Asadullah, M., et al., "Cobalt catalyzed carboxylation reaction of saturated hydrocarbons with CO in the presence of $K_2S_2O_8$ TFA under mild conditions," *Tetrahedron Lett.*, 1999, 40, 8867-8871.
Asadullah, M., et al., "Calcium-Catalyzed Selective and Quantitative Transformation of CH4 and CO into Acetic Acid," *Angew. Chem. Int. Ed.*, 2000, vol. 39, No. 14, pp. 2475-2478.
Bagno, A., et al., "Superacid-Catalyzed Carbonylation of Methane, Methyl Halides, Methyl Alcohol, and Dimethyl Ether to Methyl acetate and Acetic Acid," *J. Org. Chem.*, 1990, vol. 55, pp. 4284-4289.

Chepaikin, E., et al., "Functionalisation of methane under dioxygen and carbon monoxide catalyzed by rhodium complexes Oxidation and oxidative carbonylation" *J. Mol. Catal. A: Chem.*, 2001, vol. 169, pp. 89-98.
Fujiwara, Y., et al., "Transition metal catalyzed acetic acid synthesis from methane and carbon monoxide," *Studies in Surface Science and Catalysis*, 1998, vol. 119, pp. 349-353.
Golombok, M., et al., "A Chemical Alternative to Natural Gas Flaring," *Ind. Eng. Chem. Res.*, 2003, vol. 42, pp. 5003-5006.
Kurioka, M., et al., "Palladium-Catalyzed Acetic Acid Synthesis from Methane and Carbon Monoxide or Dioxide," *Chem. Lett.*, 1995, p. 244.
Lin, M., et al., "Direct catalytic conversion of methane to acetic acid in aqueous medium," *Nature*, 1994, vol. 368, pp. 613-615.
Mukhopadhyay, S., et al., "Direct catalytic sulfonation of methan with $SO_2$ to methanesulfonic acid (MSA) in the presence of molecular $O_2$." *Chem. Commun.*, 2003, pp. 1590-1591.
Nakata, K., et al., "Palladium (II) and/or copper (II)-catalyzed carboxylation of small alkanes such as methane and ethane with carbon monoxide," *J. Organomet. Chem.*, 1994, vol. 473, pp. 329-334.
Nishiguchi, T., et al., "Transition Metal Catalyzed Acetic Acid Synthesis from Methane and CO," *Chem. Lett.*, 1992, pp. 1141-1142.
Nizova, G., et al., "Carboxylation of methane with CO or $CO_2$ in aqueous solution catalysed by vanadium complexes," *Chem. Commun.*, 1998, pp. 1885-1886.
Periana, R., et al., "Catalytic, Oxidative Condensation of $CH_4$ to $CH_3COOH$ in One Step via CH Activation," *Science*, 2003, vol. 301, pp. 814-818.
Piao, D-G., et al., An efficient partial oxidation of methane in trifluoroacetic acid using vanadium-containing heteropolyacid catalysts, *J. Organomet. Chem.*, 1999, vol. 574, pp. 116-120.

(Continued)

Primary Examiner—Paul A. Zucker
(74) Attorney, Agent, or Firm—Townsend and Townsend and Crew LLP

(57) ABSTRACT

Acetic acid is produced by oxidation of methane with an oxygen-containing gas in the presence of an acid selected from concentrated sulfuric acid and fuming sulfuric acid, a palladium-containing catalyst and a promoter, preferably a copper or iron salt. The addition of a promoter and $O_2$ to a system that includes a palladium-containing catalyst such as $PdCl_2$ increases the rate of acetic acid formation from methane by more than an order of magnitude as compared with prior art and, in addition, inhibits the precipitation of Pd black.

24 Claims, No Drawings

OTHER PUBLICATIONS

Reis, P., et al., "Single-Pot Conversion of Methane into Acetic Acid in the Absence of CO and with Vanadium Catalysts Such as Amavadine," *Angew. Chem. Int. Ed.,* 2003, vol. 42, pp. 821-823.

Taniguchi, Y., et al., "Highly Efficient Vanadium-Catalyzed Transformation of $CH_4$ and CO to Acetic Acid," *Org. Lett.,* 1999, vol. 1, No. 4, pp. 557-559.

Yin, G., et al., "$Cu(OAc)_2$-catalyzed partial oxidation of methane to methyl trifluoroacetate in the liquid pahse," *Appl. Organomet. Chem.,* 2000, vol. 14, pp. 438-442.

Zerella, M., et al., "Direct Oxidation of Methan to Acetic Acid Catalyzed by $Pd^{2+}$ and $Cu^{2+}$ in the Presence of Molecular Oxygen," *Chem. Commun.,* 2002, pp. 1-2.

Zerella, M., et al., "Synthesis of Mixed Acid Anhydrides from Methane and Carbon Dioxide in Acid Solvents," *Organic Letters,* 2003, vol. 5, No. 18, pp. 3193-3196.

Zerella, Mark, et al., "Direct oxidation of methane to acetic acid catalyzed by $Pd^{2+}$ and $Cu^{2+}$ in the presence of molecular oxygen"; Chem. Commun., Aug. 3, 2004, together with a blank *Chemical Communications* template.

* cited by examiner

PROCESS FOR DIRECT OXIDATION OF METHANE TO ACETIC ACID

BACKGROUND OF THE INVENTION

This invention relates in general to an improved process for the production of acetic acid or a derivative thereof by liquid phase oxidation of methane. In particular the present invention relates to the liquid phase oxidation of methane with an oxidant in a strong acid in the presence of a catalyst comprising palladium combined with a promoter.

The primary process route used today for production of acetic acid is by catalytic reaction of methanol and carbon monoxide. Such a process, typically termed "carbonylation", is described in a number of patents and publications. Rhodium, palladium or iridium-containing catalysts have been found especially useful for conducting this reaction. A recent example of a patent on such a process is U.S. Pat. No. 6,472,558 of Key et al., which describes a process for reaction of methanol (and/or a reactive derivative of methanol such as methyl acetate or dimethyl ether) and carbon monoxide in a liquid reaction composition that comprises methyl acetate, methyl iodide, acetic acid, water and a polydentate phosphine oxide, in addition to the iridium catalyst.

Another process route that has been found useful for the production of acetic acid involves the catalytic oxidation of ethane and/or ethylene. Such processes are disclosed, for instance, in U.S. Pat. No. 6,383,977 of Karim et al., U.S. Pat. No. 6,399,816 of Borchert et al. and U.S. Pat. No. 6,706,919 of Obana et al. and U.S. published applications 2003/0158440 of Zeyss et al. and 2004/0031084 of Cook et al. In the processes described in these, a mixed oxide catalyst containing multiple metals such as palladium, molybdenum, vanadium, niobium, antimony, nickel, calcium, and others, is used.

Methane is the lowest molecular weight, and simplest in structure, of the hydrocarbons. Because of the existence of large reserves of methane worldwide it has been considered desirable for some time to develop processes to convert methane to more valuable chemicals. Processes for production of acetic acid from methanol represent an ultimate use of methane, but in current commercial practice, the methane first must be converted to methanol. A process that produces acetic acid directly from methane would be more desirable.

A small amount of work has been conducted so far on the direct conversion of methane to acetic acid, for instance by reaction of methane with carbon dioxide. A process for production of acetic acid by such a reaction was disclosed in the 1924 British patent 226,248 of Dreyfus. The patent describes a process involving gas phase reaction of methane with carbon monoxide and/or carbon dioxide in the presence of a catalyst that preferably contains nickel carbonate. Apparently a mixture of acetic acid, acetaldehyde and possibly acetone is obtained. No data on yields or conversions is contained in this patent.

PCT application WO 96/05163 of Hoechst A. G. describes a gas phase reaction of methane and carbon dioxide to produce acetic acid, using a catalyst containing one or more Group VIA, VIIA and/or VIIIA metals. Selectivities of 70–95% based on methane are asserted; however the application contains no exemplary data.

A number of researchers have investigated production of acetic acid by liquid phase carbonylation of methane with carbon monoxide, due to the favorable thermodynamics of this reaction. See, for instance, Bagno, et al. *J. Org. Chem.* 1990, 55, 4284–4289; Lin, et al., *Nature* 1994, 368, 613–615, Chaepaikin, et al., *J. Mol. Catal. A: Chem.* 2001, 169, 89–98; Nishiguchi, et al., *Chem. Lett.* 1992, 1141–1142; Nakata, et al. *J. Organomet. Chem.* 1994, 473, 329–334; Kurioka, et al., *Chem. Lett.* 1995, 244; Fujiwara, et al., *Studies in Surface Science and Catalysis* 1998, 119, 349–353; Taniguchi, et al., *Org. Lett.* 1999, 1 (4), 557–559; Asadullah, et al., *Tetrahedron Lett.* 1999, 40, 8867–8871; Nizova et al., *Chem. Commun.* 1998: 1885; Piao et al., *J. Organomet. Chem.* 1999, 574, 116–120; Yin et al., *Appl. Organomet. Chem.* 2000, 14, 438–442; Reis et al., *Angew. Chem. Int. Ed.* 2003, 42, 821; and Asadullah, et al., *Chem. Int. Ed.* 2000, 39 (14), 2475–2478.

Recently, Periana et al., *Science*, 2003, 301, 814 reported an experiment in which acetic acid was directly prepared from methane in the presence of palladium sulfate in concentrated sulfuric acid without the addition of COX. Acetic acid and methyl bisulfate were the reaction products. Hydrolysis of these yields acetic acid and an equilibrium mixture of methyl bisulfate and methanol. After 7 h of reaction at 180° C., 82 mM acetic acid and 38 mM methanol were ultimately formed. The reaction as reported was 90% selective to these products, with the only byproduct being $CO_2$. The overall stoichiometry of the reaction is given as:

$$2CH_4 + 4H_2SO_4 \rightarrow CH_3COOH + 4SO_2 + 6H_2O.$$

However, this process displayed a serious drawback. During the reaction particles of palladium black were formed due to the reduction of Pd(II) to Pd(0). This results in loss of catalytic activity due to loss of soluble palladium. A further drawback to the process is that it consumes sulfuric acid and produces $SO_2$ as a by-product, which is either wasted or can be recycled back to sulfuric acid via a number of processing steps including reaction with oxygen to give $SO_3$ which is then reacted with water to give sulfuric acid. It would be desirable to provide a process for production of acetic acid from methane using a palladium catalyst where the catalytic benefits of palladium salts are retained but without the disadvantages of palladium black formation. It would also be desirable to reduce the number of processing steps.

BRIEF SUMMARY OF THE INVENTION

This invention comprises a process for the production of acetic acid, or derivatives such as methyl acetate and acetyl sulphate, from methane, by contacting a methane-containing feed with an oxidant in the presence of a palladium-containing catalyst, a promoter, and an acid selected from concentrated sulfuric acid and fuming sulfuric acid. The process may be conducted in one step or two, as described below. Derivatives of acetic acid that may be produced include methyl acetate, acetyl sulfate and methyl bisulfate.

DETAILED DESCRIPTION OF THE INVENTION

According to the invention, acetic acid is produced from methane by contacting the methane, in a feed comprising methane and optionally other components, with an oxygen-containing gas in the presence of a palladium-containing catalyst, a promoter, and an acid selected from concentrated sulfuric acid and fuming sulfuric acid. The inclusion of a promoter, for example a copper (II) salt, increases the rate of acetic acid formation from methane by more than a factor of five as compared with the Periana et al. work and, in addition, inhibits the precipitation of Pd black.

The methane that is introduced into the process may be an essentially pure methane stream, a methane stream that contains various impurities, or a stream that contains methane as one of several components, for example, a methane-containing stream that emanates from a chemical process unit, a natural gas stream, a methane-containing stream produced by a gas generator, a methane-containing off-gas, a biogenic methane stream, and the like. The methane feed to the process may also contain other materials that may be oxidized under the process conditions to form acetic acid, e.g. ethane, propane, butane and higher hydrocarbons. Methanol, dimethyl ether, methyl acetate and methyl bisulfate may also be fed to the process.

The palladium-containing catalyst may be any palladium-containing material that possesses the necessary catalytic activity for this reaction. Preferred palladium-containing catalysts are palladium salts such as palladium (II) and palladium (IV) sulfates, chlorides, nitrates, acetates, acetylacetonates, amines, oxides, and ligand-modified palladium systems, for example systems containing ligands such as phosphines, nitriles, and amines, for example triphenylphosphine, diphenylphosphinopropane, bipyrimidine, bipyridine, acetonitrile, and benzonitrile.

Promoters suitable for use in the process of this invention include materials that have a demonstrated REDOX couple with palladium, such as salts of copper, silver, gold, vanadium, niobium, tantalum, iron, chromates, and organic systems such as hydroquinone or anthraquinone complexes with such metals. Preferred promoters for the process are salts of copper and iron, most preferably cupric salts. Other preferred promoters include cupric and cuprous nitrate, sulfate, phosphate, acetate, acetylacetonate, and oxide, ferric chloride and ferric sulfate. For metals that have multiple valences, e.g. copper and iron, the promoter can be introduced as a salt of the lower valence (e.g., cuprous chloride, ferrous chloride), which becomes oxidized in situ when in contact with the oxygen-containing gas or with $H_2SO_4$ or $SO_3$. In addition to its primary function, the promoter may also serve to catalyze regeneration of the acid. Additionally, a salt of platinum or mercury may be included in the process, to assist in conversion of methane to methanol and/or methyl bisulfate, which may then be converted to acetic acid by the catalyst/promoter.

The molar ratio of palladium-containing catalyst to promoter can vary but is preferably within the range from about 50:1 to about 1:5, and most preferably from about 20:1 to about 1:5. In one preferred embodiment the catalyst and promoter are used in equimolar amounts.

As with the Periana et al. process, the primary products are acetic acid and methanol. When the process was run for 4 hours under conditions identical to those used in Periana et al., the acetic acid yield was 9 mM. With the inclusion of a cupric salt and oxygen, the acetic acid production increased to 49 mM. However, whereas Periana et al. reported methanol production for a 4 hour reaction to an extent about the same as that of the acetic acid, the process of this invention typically produced substantially higher ratios of acetic acid to methanol, as will be seen in Table 1 below. In addition, the ratio of the two products can be enhanced further by increasing the residence time, methane pressure, oxygen pressure, or reaction temperature.

Additionally, when the process is operated with palladium and a cupric salt in the absence of an oxygen-containing gas, no Pd black precipitate was observed, evidencing the advantageous effect of the copper compound in reducing the loss of activity of the whole process—see example 2 below.

Process temperatures in general may be from about 100 to about 300° C., most preferably from about 110 to about 220° C. Suitable reaction pressures range from about 1 to about 200 barg, preferably from about 20 to about 80 barg.

The reaction is conducted in the presence of an acid, in which the catalyst and promoter are dissolved. The acid is preferably concentrated sulfuric acid or fuming sulfuric acid. The process is generally carried out by bubbling the methane-containing feed and the oxygen-containing gas, or otherwise introducing them, into the acid, with the latter containing the catalyst and promoter. The oxygen-containing gas may be introduced together with the methane-containing feed, or separately from it. If the two are introduced separately, their flow may be concurrent or countercurrent. The apparatus or equipment used for the process may be any type of suitable reactor, together with associated equipment, for example, for handling materials flowing into and out of the reactor, recycle streams, waste streams, etc. The reactor may include an agitator to aid in the mixing of the reactants. All parts of the apparatus will be constructed from appropriate materials.

The oxidant used in the process is preferably an oxygen-containing gas which may be in the form of molecular oxygen, a commercial mixture of molecular oxygen with an inert gas such as nitrogen, oxygen-enriched air, or air, but is most preferably substantially pure oxygen or a commercial mixture that contains predominantly oxygen. The partial pressure of methane is suitably in the range of about 0.5 barg to about 100 barg, preferably about 10 to about 50 barg, and the partial pressure of the di-oxygen ($O_2$) is likewise suitably in the range about 0.5 barg to about 100 barg, preferably about 3 to about 50 barg. The ratio of methane to $O_2$ is preferably outside the flammable region.

The primary products of the reaction are acetic acid, methyl bisulfate, methanol, and methanesulfonic acid. Water may be added after the completion of the reaction to hydrolyze any anhydrides and/or esters. The methanol, methyl bisulfate, and methanesulfonic acid can be recycled to the oxidation reactor.

The process may be conducted as a batch or continuous process, as desired, with appropriate equipment. It may be conducted as a single-step process, batch or continuous, with all substances introduced into and removed from a single reactor, or as a two-step process, in which the process is preferably conducted as a continuous process. In a two-step process, for instance, the methane, acid, catalyst and promoter are contacted in the first stage and the reaction products of that stage are passed to a second stage (for example a second reactor or a second portion of a reactor) in which they are contacted with the oxygen-containing gas. Alternately, both steps may be carried out in the same reactor, with methane and oxygen feeds being introduced separately, spaced apart timewise. A two-stage operation may provide an opportunity for regeneration of the promoter and/or the acid by the oxygen-containing gas, and, by separating the oxygen- and methane-containing gas feeds, may minimize overoxidation of methane to carbon oxides.

EXAMPLES

Example A (comparative example)

This example demonstrates the production of acetic acid from methane in concentrated sulfuric acid in the presence of a palladium catalyst, but without the inclusion of either a promoter or an oxygen-containing gas.

0.402 g $PdSO_4$ and 35.9 g $H_2SO_4$ were introduced into a tantalum autoclave. Then, the autoclave was closed and pressure tested with 65 barg of nitrogen. The autoclave was then pressurized with $CH_4$ (approximately 55 barg) and heated to 180° C. while stirring the mixture with a magnetic stirrer. The temperature of the reaction mixture was kept at about 180° C.±5 throughout the experiment (4 hours) by means of heating cartridges connected to a Eurotherm™ control system.

After 4 hours, the reactor pressure was found to have increased by 61.6 barg to 63.0 barg. After cooling the autoclave to room temperature, the system was vented and the autoclave was removed from the pressure system. A dark liquid with a black precipitate was collected from the autoclave. The acetic acid was quantified by HPLC; the methanol was quantified using $^1$H-NMR spectroscopy.

The charge composition and product distribution data obtained are given in Table 1.

Example B

This example demonstrates the production of acetic acid from methane in concentrated sulfuric acid in the presence of a palladium catalyst and a copper promoted and the absence of an oxygen-containing gas.

In this example, 0.418 g $PdSO_4$, 1.567 g $CuSO_4$ and 36.2 g of 96% (on a weight basis) $H_2SO_4$ were introduced into a tantalum autoclave. Then, the autoclave was closed and pressurized with methane (approximately 55 barg). The experiment was then conducted as for comparative example A.

After 4 hours, the reactor pressure was found to have increased from 65.9 barg to 66.3 barg. After cooling the autoclave to room temperature, the system was vented and the autoclave was removed from the pressure system. A light brown liquid with a white precipitate was collected from the autoclave. Compared to the experiment without $CuSO_4$ the Pd black formed was greatly reduced. The acetic acid was quantified by HPLC; the methanol was quantified using $^1$H-NMR spectroscopy.

The charge composition and product distribution data obtained are given in Table 1.

TABLE 1

| Example | $PdSO_4$ (grams) | $CuSO_4$ (grams) | $CH_4$ (barg) | $H_2SO_4$ (grams) | AcOH (ppm) | MeOH (ppm) |
|---|---|---|---|---|---|---|
| A | 0.402 | — | 54.4 | 35.9 | 2900 | 900 |
| B | 0.418 | 1.567 | 55.8 | 36.2 | 570 | 750 |

Temperature = 180° C., Experiment time 4 hours.

Example C

In this example $CH_4$ and $O_2$ were reacted at 180° C. in a high pressure, glass-lined autoclave containing catalytic amounts of $PdSO_4$ and $CuCl_2$ added to concentrated sulfuric acid (96% w/w). Reactions were carried out for 4 h, after which an equal volume of water was added to the product solution in order to hydrolyze any anhydrides. Reaction products were analyzed by $^1$H NMR.

More specifically, using a 50 mL glass autoclave liner, 0.0121 g (20 mM) of $PdSO_4$, and 0.0081 g (20 mM) of $CuCl_2$ were dissolved in 3 mL (5.67 g) of 96% sulfuric acid. A small Teflon-coated stir bar was added prior to sealing the autoclave. The reactor was purged with Ar and then pressurized with 400 psig of $CH_4$ and 30 psig of $O_2$. The reactor was heated to 180° C. and maintained for 4 h. Upon completion of the reaction, the reactor was quenched in ice water to <35° C. and then vented. Upon opening the reactor, 3 mL of water were added to the product mixture.

For $^1$H NMR analysis, $D_2O$ was used in a capillary as the lock reference. The corresponding chemical shift for acetic acid was 2.0 to 2.1 ppm, depending on the concentrations of the products. The corresponding chemical shifts for methanol and methyl bisulfate were 3.3 to 3.4 and 3.6 to 3.7, respectively. Two unidentified byproducts appear in the $^1$H NMR spectrum at 4.0 to 4.1 ppm and 4.4 to 4.5 ppm. The peaks are consistently smaller than that for methanol.

In the autoclave and under reaction conditions identical to those used by Periana et al., i.e. without including oxygen or a cupric salt, the products were 9 mM $CH_3COOH$ and 7 mM $CH_3OH$. This is about a factor of five lower than that reported by Periana et al. The carbon selectivity to acetic acid and methanol was measured and found to be 65%. $SO_2$ was not detected in the gas phase, possibly due to relatively low amounts produced and its high solubility in sulfuric acid. At the end of the 4-h reaction period, Pd particles were found at the bottom of the reaction vessel.

Using the process of the invention, i.e., when Cu(II) and molecular oxygen were added to the reaction mixture, acetic acid production increased to 49 mM but the methanol concentration remained low at 4 mM. Methanesulfonic acid was also observed as one of the products (5 mM). However, in contrast to what was found in the absence of Cu(II) and $O_2$, the reaction solution retained its light red color. The autoclave head space contained both CO and $CO_2$. The carbon selectivity to acetic acid and methanol was determined to be 47%.

Using the Pd/Cu/$O_2$ mixture, the effect of reaction conditions was evaluated with the aim of maximizing the acetic acid yield. Table 1 presents the results of varying Cu to Pd ratio, time, temperature, oxygen pressure, and methane pressure. Entries 1 and 2 demonstrate that Pd is required for the formation of products, whereas a comparison of entries 1, 3, and 4 shows that the yield of acetic acid decreases and the yield of methanol increases with increasing Cu:Pd ratio. Entries 5–9 indicate that longer reaction times and higher reaction temperatures increase the yield of acetic acid production but do not strongly influence the yield of methanol. Comparison of entries 1, 10, and 11 shows that the yield of acetic acid increases strongly with increasing $O_2$ partial pressure, as does the yield of acetic acid relative to methanol, suggesting that methanol derivatives are an intermediate in the formation of acetic acid. The effect of methane partial pressure can be seen by examining entries 1, 12, and 13. As one would expect, the yields of both acetic acid and methanol increase with increasing methane pressure. In fact, the best acetic acid production, 132 mM, was achieved using 600 psig of methane.

TABLE 2

Effect of Varied Reaction Conditions on the Product Distributions

| Example | $PdSO_4$ (mM) | $CuCl_2$ (mM) | t (h) | T (° C.) | $O_2$ (psig) | $CH_4$ (psig) | AcOH (mM) | MeOH (mM) |
|---|---|---|---|---|---|---|---|---|
| 1 | 20 | 20 | 4 | 180 | 30 | 400 | 49 | 3.7 |
| 2 | 0 | 20 | 4 | 180 | 30 | 400 | 0 | 0 |
| 3 | 20 | 6.7 | 4 | 180 | 30 | 400 | 66 | 2.1 |
| 4 | 20 | 60 | 4 | 180 | 30 | 400 | 11 | 6.9 |
| 5 | 20 | 20 | 2 | 180 | 30 | 400 | 44 | 4.7 |
| 6 | 20 | 20 | 6 | 180 | 30 | 400 | 106 | 4.5 |
| 7 | 20 | 20 | 4 | 160 | 30 | 400 | 45 | 5.7 |

TABLE 2-continued

Effect of Varied Reaction Conditions on the Product Distributions

| Example | PdSO$_4$ (mM) | CuCl$_2$ (mM) | t (h) | T (° C.) | O$_2$ (psig) | CH$_4$ (psig) | AcOH (mM) | MeOH (mM) |
|---|---|---|---|---|---|---|---|---|
| 8  | 20 | 20 | 4 | 140 | 30  | 400 | 18  | 63  |
| 9  | 20 | 20 | 4 | 120 | 30  | 400 | 4.4 | 37  |
| 10 | 20 | 20 | 4 | 180 | 0   | 400 | 2.5 | 3.6 |
| 11 | 20 | 20 | 4 | 180 | 150 | 400 | 73  | 2.3 |
| 12 | 20 | 20 | 4 | 180 | 30  | 200 | 27  | 1.7 |
| 13 | 20 | 20 | 4 | 180 | 30  | 600 | 132 | 7.2 |

Reaction Conditions (unless otherwise noted): 3 mL 96% H$_2$SO$_4$; 20 mM PdSO$_4$; 20 mM CuCl$_2$; 400 psig CH$_4$; 30 psig O$_2$; 180° C.; 4 h.

Example D

A 50-mL glass-lined autoclave reactor was charged with 3 mL of 96% sulfuric acid, and 0.0121 g (20 mM) of PdSO$_4$ and 0.0121 (20 mM) of AgCl$_2$ were added. The autoclave reactor was purged with Ar and then pressurized with 400 psig of CH$_4$ and 30 psig of O$_2$. The reactor was heated to 180° C. and maintained for 4 h. Upon cooling and then opening the reactor, 3 mL of water were added to the product mixture. $^1$H NMR analysis was used to quantify the products formed, and it was thereby confirmed that 54 mM acetic acid and 1.7 mM methanol had been formed under these reaction conditions.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A process for the production of acetic acid from methane comprising contacting a methane-containing feed with an oxygen-containing gas in the presence of a palladium-containing catalyst, a promoter, and an acid selected from concentrated sulfuric acid and fuming sulfuric acid.

2. A process according to claim 1 in which the palladium-containing catalyst is selected from palladium salts, palladium oxides, and ligand-modified palladium systems.

3. A process according to claim 1 in which the palladium-containing catalyst is selected from palladium (II) and palladium (IV) sulfates, chlorides, nitrates, acetates, acetylacetonates, amines, oxides, and ligand-modified palladium-containing systems wherein the ligand is selected from phosphines, nitriles, and amines.

4. A process according to claim 1 in which the promoter is selected from copper, silver, gold, vanadium, niobium, tantalum, or iron salts, chromate salts, and hydroquinone or anthraquinone complexes with said metals.

5. A process according to claim 1 in which the promoter is selected from salts of copper and iron.

6. A process according to claim 5 in which the promoter is selected from cupric salts, cuprous salts, and ferric salts.

7. A process according to claim 5 in which the promoter is selected from cupric and cuprous chlorides, nitrates, sulfates, phosphates, acetates, acetylacetonates, and oxides, ferric chloride and ferric sulfate.

8. A process according to claim 5 in which the promoter is cupric chloride.

9. A process according to claim 1 in which the molar ratio of palladium-containing catalyst to promoter is from about 50:1 to about 1:5.

10. A process according to claim 1 in which the molar ratio of palladium-containing catalysts to promoter is from about 20:1 to about 1:5.

11. A process according to claim 1 in which the temperature is from about 100 to about 300° C.

12. A process according to claim 1 in which the temperature is from about 110 to about 220° C.

13. A process according to claim 1 in which the acid is concentrated sulfuric acid.

14. A process according to claim 1 in which the acid is fuming sulfuric acid.

15. A process according to claim 1 further comprising adding water to the reaction products to accomplish hydrolysis of one or more of the reaction products.

16. A process according to claim 1 in which the oxygen-containing gas comprises a commercial mixture of oxygen containing primarily molecular oxygen and an inert gas.

17. A process according to claim 1 in which the methane partial pressure is from about 0.5 barg to about 100 barg.

18. A process according to claim 1 in which the partial pressure of the oxygen in the oxygen-containing gas is from about 0.5 barg to about 100 barg.

19. A batch process according to claim 1.

20. A continuous process according to claim 1.

21. A process according to claim 1 conducted in one stage.

22. A process according to claim 1 conducted in two stages.

23. A process according to claim 22 in which the methane-containing feed is contacted with the catalyst, promoter and acid in the first stage, and the products from the first stage are contacted with the oxygen-containing gas in the second stage.

24. A continuous process according to claim 21.

* * * * *